US009925167B2

(12) United States Patent
Kalbe et al.

(10) Patent No.: US 9,925,167 B2
(45) Date of Patent: Mar. 27, 2018

(54) AGENTS FOR THE CONTROL OF PARASITES ON ANIMALS

(75) Inventors: Jochen Kalbe, Leichlingen (DE); Olaf Hansen, Leverkusen-Hitdorf (DE)

(73) Assignee: Hansen-AB GmbH, Leverkusen (DE)

( * ) Notice: Subject to any disclaimer, the term of this patent is extended or adjusted under 35 U.S.C. 154(b) by 186 days.

(21) Appl. No.: 14/128,773

(22) PCT Filed: Jun. 28, 2012

(86) PCT No.: PCT/EP2012/002712
§ 371 (c)(1),
(2), (4) Date: Feb. 26, 2014

(87) PCT Pub. No.: WO2013/000572
PCT Pub. Date: Jan. 3, 2013

(65) Prior Publication Data
US 2015/0038537 A1    Feb. 5, 2015

(30) Foreign Application Priority Data
Jun. 30, 2011  (EP) .................................... 11005341

(51) Int. Cl.
| | | |
|---|---|---|
| *A61K 31/4418* | (2006.01) | |
| *A61K 31/355* | (2006.01) | |
| *A01N 47/02* | (2006.01) | |
| *A61K 9/00* | (2006.01) | |
| *A61K 31/277* | (2006.01) | |
| *A61K 31/415* | (2006.01) | |
| *A61K 45/06* | (2006.01) | |
| *A61K 47/14* | (2017.01) | |
| *A61K 47/22* | (2006.01) | |

(52) U.S. Cl.
CPC ............ *A61K 31/355* (2013.01); *A01N 47/02* (2013.01); *A61K 9/0017* (2013.01); *A61K 31/277* (2013.01); *A61K 31/415* (2013.01); *A61K 45/06* (2013.01); *A61K 47/14* (2013.01); *A61K 47/22* (2013.01)

(58) Field of Classification Search
USPC ........................................................ 514/345
See application file for complete search history.

(56) References Cited

U.S. PATENT DOCUMENTS

| | | | |
|---|---|---|---|
| 6,303,651 B1* | 10/2001 | Hersh .................... A61K 33/04 424/641 |
| 7,419,936 B2* | 9/2008 | Plant et al. .................... 504/193 |
| 8,003,650 B2* | 8/2011 | Jachmann et al. ........ 514/252.05 |
| 8,367,088 B2 | 2/2013 | Kelley | |
| 2003/0187029 A1 | 10/2003 | Valdez et al. | |
| 2011/0071193 A1 | 3/2011 | Nouvel | |
| 2011/0165094 A1* | 7/2011 | Panin .............................. 424/43 |
| 2014/0170199 A1* | 6/2014 | Flochlay-Sigognault et al. ............................. 424/411 |

FOREIGN PATENT DOCUMENTS

| | | |
|---|---|---|
| WO | 2008/030385 A2 | 3/2008 |
| WO | 2009/027506 A2 | 3/2009 |
| WO | 2010/031584 A2 | 3/2010 |

OTHER PUBLICATIONS

Lotion crafters, LLC., http://www.lotioncrafter.com/vitamin-e-acetate.html.*
Baschong, W. et al., Direct Evidence for Bioconversion of Vitamin E acetate into vitamin E: An ex vivo study in viable human skin. Journal of Cosmetic Science, May 1, 2001, 52(3):155-161 (Abstract).*
Kamimura, M. The Journal of Vitaminology 18, 204-209 (1972). "Antiinflammatory Activity of Vitamin E".*
International Search Report for corresponding PCT/EP2012/002712 dated Oct. 30, 2012, four pages.
"238 deltamethrin," The Pesticide Manual—World Compendium, 15th Edition, Jan. 1, 2009, pp. 313-315.
International Preliminary Report on Patentability for corresponding PCT/EP2012/002712 dated Jan. 16, 2014, 15 pages.

* cited by examiner

*Primary Examiner* — Sreenivasan Padmanabhan
*Assistant Examiner* — Y Jeanmarie Z Calvillo
(74) *Attorney, Agent, or Firm* — Rankin, Hill & Clark LLP

(57) ABSTRACT

The invention relates to agents for the control of parasites on animals, comprising an active substance from the group of the phenylpyrazoles and vitamin E or a derivative thereof, such as particularly vitamin E acetate, as well as optionally a further active substance from the group of the pyrethroids and/or optionally additionally further active and/or auxiliary substances. In particular, the invention relates to the use of such agents for the control of ectoparasites such as, in particular, fleas, ticks and sand flies in pets such as, in particular, in dogs, cats and ferrets.

8 Claims, No Drawings

AGENTS FOR THE CONTROL OF PARASITES ON ANIMALS

The invention relates to agents for the control of parasites on animals, comprising an active substance from the group of the phenylpyrazoles and vitamin E or a derivative thereof, such as particularly vitamin E acetate, as well as optionally a further active substance from the group of the pyrethroids and/or optionally additionally further active and/or auxiliary substances. In particular, the invention relates to the use of such agents for the control of ectoparasites such as, in particular, fleas, ticks and sand flies in pets such as, in particular, in dogs, cats and ferrets.

INTRODUCTION AND PRIOR ART

Numerous agents for the control of parasites such as, in particular, ectoparasites, are known from the prior art which are based on active substances from the group of the phenylpyrazoles, optionally also in combination with further active substances, for example from the group of the pyrethroids, or with auxiliary substances, such as spreading agents and solvents. In particular, the addition of auxiliary substances from the group of the antioxidants to such agents for the control of parasites is known from the prior art, which is significant particularly when lipophilic, or fat-, oil- or wax-containing auxiliary substances or active substance formulations are used. Among others, a common and familiar antioxidant is tocopherol or tocopheryl nicotinate from the group of the vitamin E compounds, which is customarily used in quantities <1% by wt., or up to maximally 10% by wt.

In particular, it is also already known from the prior art that phenylpyrazole derivatives, such as fipronil, and pyrethroid derivatives, such as deltamethrin or flumethrin, are effective agents for the control of parasites in animals.

Fipronil is a phenylpyrazole derivative (1-[2,6-Cl$_2$-4-CF$_3$-phenyl]-3-CN-4-[SO—CF$_3$]-5-NH$_2$-pyrazole) and corresponds to the general formula

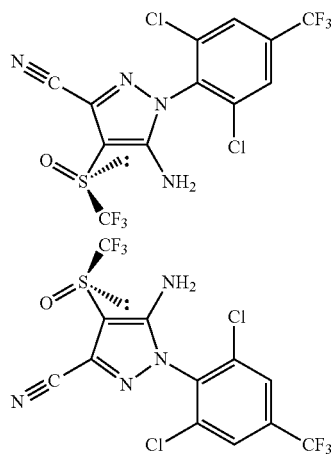

Fipronil is used, in particular, in applications in farming and animal health in the control of parasites, such as anthropodes, menatodes, helminths and protozoa, but also against ectoparasites, such as fleas, lice and ticks, and is mentioned in the patents EP 295117, U.S. Pat. No. 5,232,940, EP 352944 and GB 2457734, for example.

Flumethrin (α-cyano(4-fluoro-3-phenoxyphenyl)methyl 3-[2-chloro-2-(4-chlorophenyl)ethenyl]-2,2-dimethylcyclopropanecarboxylate), in

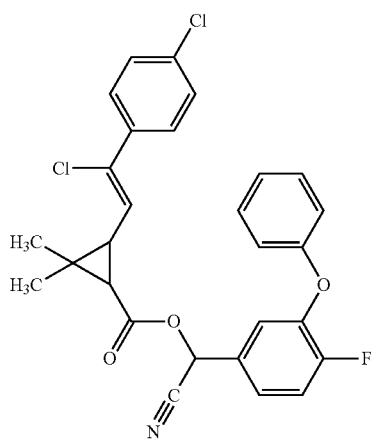 [SMILES: CC1(C)C(/C=C(\Cl)c2ccc(Cl)cc2)C1C(=O)OC(C#N)c1ccc(F)c(Oc2ccccc2)c1]

accordance with the general formula and deltamethrin (also referred to as decamethrin or (1R,3R)-[(S)-α-cyano-3-phoxybenzyl-3-(2,2-dibromovinyl)]-2,2-dimethylcyclopropanecarboxylate), in accordance with the general formula

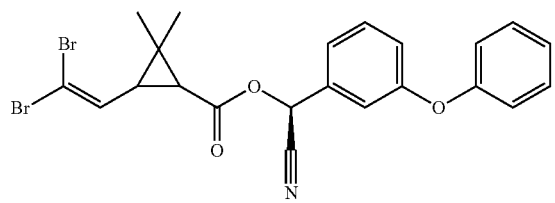

are type II pyrethroid derivatives and fast-acting contact poisons (nerve poisons) which lead to the Na$^+$ channels of the nerve cells not closing anymore, which causes Na$^+$ ions to flow into the interior of the cell without hindrance and the occurrence of uncontrollable nerve impulses. In the case of anthropodes, for example, this triggers a knockdown effect which rapidly takes effect. Compared to the natural pyrethrins, this effect is substantially longer-lasting because of the better stability of flumethrin and deltamethrin. Both flumethrin and deltamethrin moreover possess distinct repelling properties. They are based upon an irritation of tactile elements in the extremities (foot retraction effect) of the anthropodes. In the case of ticks, an inhibition of the egg deposition occurs in addition to the killing effect, so that surviving female ticks are incapable of producing viable progeny.

Both flumethrin and deltamethrin are known for their irritating action on sensitive areas of the skin, the mucosa and eyes, so that localized pruritus and erythema development accompanied by the development of alopecia may occur.

In order to attain an improvement of pest control agents both with respect to acute efficacy as well as the effective period, numerous combination preparations have been developed in the past. For example, various combination preparations based on pyrazoles, such as fipronil, with other active substances, or of pyrethroids, such as flumethrin or deltamethrin, with other active substances have also been described.

US 2002/0090387 and U.S. Pat. No. 5,567,429, for example, relate to the combination of fipronil with insect growth regulators (IGRs) for the optimized control of fleas in dogs and cats. Methoprene, pyriproxyfen, hydroprene, lufeneron, triflumuron and fenoxycarb, for instance, are mentioned as IGRs. On the one hand, adult parasites are killed, and on the other hand, further growth of eggs and larvae is inhibited through two different mechanisms (GABA inhibition and growth inhibition of the larvae) by the combination of these classes of active substances.

US 2003/0050327 describes the combination of phenylpyrazoles, such as, among others, fipronil, with macrolide derivatives (macrocyclic lactones) such as ivermectin, avermectin and moxidectin in spot-on applications.

DE 4 414 333 discusses the possibility, in principle, of combining active substances for parasite control, also of combining pyridylpyrazoles with e.g. marcolides, IGRs, phosphoric acid esters or even pyrethroids. However, the group of the pyridylpyrazoles does not include the phenylpyrazole-derivative fipronil, which is particularly preferred according to the invention. The pyrethroids mentioned in this document comprise, for example, deltamethrin, whereas no explicit mention is made of flumethrin.

U.S. Pat. No. 5,232,940, which was already mentioned above, also includes fipronil, among others, in comprehensive lists of effective phenylpyrazoles (compound no. 52). The phenylpyrazoles mentioned herein can, in principle, also be combined in numerous possible combinations with various other compounds that are effective against parasites, the list of such other possible active substances also comprising active substances from the group of the pyrethroids, particularly also deltamethrin. No explicit mention is made of flumethrin.

Combination preparations of fipronil with pyrethroids, such as deltamethrin, among others, are also disclosed in U.S. Pat. No. 6,472,417, with it describing only the use as an insecticide against termites.

WO 2001/35739, just like the associated priority application DE 19954394, relate to spot-on preparations based particularly on pyrethroids, in particular flumethrin, with deltamethrin also being mentioned as a matter of principle. In this case, the patent family in particular relates to the provision of suitable active substance formulations for the pyrethroid active substances, which are poorly soluble in water. The pyrethroids can be combined with various other active substances, amongst which N-phenylpyrazoles, for example also fipronil, are also mentioned in principle as possible compound active substances. The exemplary embodiments exclusively concern combination preparations based on flumethrin in combination with nicotinyl insecticides. A specific combination of pyrethroids, such as flumethrin or deltamethrin, with an active substance from the group of the N-phenylpyrazoles is not disclosed in the exemplary embodiments.

Other documents, such as US 2002/0177597, EP 2039248, WO 1998/23158, WO 2004/064522, WO 2009/071212 or WO 2010/026370, relate to combination preparations based on select specific active substances or compound classes in combination with known active substances comprising the groups of the pyrethroids (e.g. deltamethrin, flumethrin) and the pyrazoles (e.g. fipronil). Specific combinations of pyrethroids and pyrazoles are not disclosed in them.

Preparations based on a combination of pyrazoles and pyrethroids for the control of ectoparasites, such as ticks and fleas, are the subject matter, for example, of WO 2008/080542 or DE 102006061538, in which the list of pyrazoles also comprises, among others, fipronil, and the list of pyrethroids also comprises, among others, deltamethrin and flumethrin. Specific exemplary embodiments in which fipronil is selected as a pyrazole are not disclosed. These documents also primarily relate to the provision of suitable active substance formulations for the poorly soluble pyrethroid active substances.

Furthermore, EP 1624756 relates to combination preparations based on pyrethrins or pyrethroids in combination with the synergist MGK 264 (7-methano-1H-isoindole-1,3 (2H)-dione), with flumethrin being mentioned as a preferred pyrethroid active substance. Such combination preparation can, in principle, contain other active substances, such as pyrazoles, with fipronil, for example, also being mentioned in the list of the pyrazoles. Specific exemplary embodiments merely relate to combinations of flumethrin with imidacloprid or thiamethoxam or thiacloprid, i.e. with active substances from the group of the neonicotinoids, but not with those from the group of the pyrazoles.

In order to apply partially poorly water-soluble active substances, particularly those from the group of the pyrethroids and pyrethrins, in the form of dermally applicable liquid formulations, it is necessary to prepare homogenous solutions or emulsions based on organic solvents and insecticidal active substances. For this purpose, the active substances are dissolved most frequently in organic solvents such as isopropanol, 2-butoxy-ethylacetate, ethylene glycol diacetate, and optionally mixed with other additives. The preparation of such formulations is described in U.S. Pat. No. 4,874,753, EP 137627 and GB 2135886. If, for example, active substances from the class of the pyrethrins and pyrethroids are used, in particular α-cyano pyrethroids, the disadvantages of said systems are that they lead to severe irritation of the skin and that, moreover, they have a poor long-term action.

In order to remedy said disadvantage of, for example, the known pyrethroids and pyrethrins, AU 627847 and EP 413610 propose that these active substances be dissolved in high-boiling solvents, such as monopropylene glycol, which additionally contain skin-compatible oils such as pine oil, sunflower oil or soybean oil.

It is apparent from WO 1991/13545 that very effective, skin-compatible liquid formulations can be prepared by dissolving said active substances in quantities of >50% in aliphatic solvents, such as 2-(2-butoxyethoxyl)ethanol or 2-(2-methoxy-ethoxy)ethanol. The drawback of these formulations is that they require the use of larger active substance quantities and moreover lead to skin irritations in sensitive animal breeds.

In order to achieve an acceptable biological action when using small active substance quantities, the use of emulsions based on said active substances with the long-chained, aliphatic amines or alcohols, such as hexadecane-1-ol, 1-octadecylamine is proposed in the US patent specification U.S. Pat. No. 5,466,458. The use of the long-chained amines is disadvantageous in that they degrade said active substances over time. In most cases, the formulations based on long-chained alcohols have no sufficient long-term action.

Furthermore, WO 2001/35739 proposes to combine the pyrethroids, in particular α-cyano pyrethroids, which are critical with regard to skin irritations, with polysiloxanes which additionally contain quaternary ammonium groups. However, this type of preparation is disadvantageous in that it requires the use of larger pyrethroid quantities.

This fact can lead to incompatibilities with the target animals or the environment in many cases.

Moreover, it can also be learned from the literature that synthetic or natural pyrethroids can be combined with organic synergists, such as piperonylbutoxide (PBC)), (2-(2-ethylhexyl)-3a,4,7,7a-tetrahydro-4,7-methano-1H-isoindole-1,3(2H)-dione (MGK 264), S,S,S-tributylphosphorotrithioate (DEF) or synepirin [e.g. JOURNAL OF ECONOMIC ENTOMOLOGY, (1994 August) 87 (4) 879-84, 1994; JOURNAL OF ECONOMIC ENTOMOLOGY, (1987 August) 35 80 (4) 728-32 or Chemosphere, (November, 1997) Vol. 35, No. 10, pp. 2365-2374. ISSN: 0045-6535, Japanese Journal of Sanitary Zoology, (1995) Vol. 46, No. 1, pp. 25-30. ISSN: 0424-7086. 1995, and J ECON ENTOMOL, (1987) 80 (6), 1117-1121. CODEN: JEENAI. ISSN: 0022-0493. 1987)]. Moreover, it can be learned from the literature cited above that the efficacy of the pyrethroid-containing preparations against adult fleas can be improved if pyrethroids are combined with said synergists in quantities of 1:5, up to maximally 1:20.

Moreover, it is known, for example, from DEP. ENTOMOL., UNIV. GEORGIA, COASTAL PLAIN EXP. STN., TEFLON, GA. 31793 or India Chemosphere, (1998) 36/15 (3055-3060) 1998], that a maximum increase of efficacy is attained at a quantity ratio of active substance to synergist of 1:5 (e.g. in the case of permethrin/MGK-264 or fenvalerate/PBO).

Moreover, it is known that shampoos containing dipropylpyridine-2,5-dicarboxylate, MGK 264, piperonyl-butoxide, and pyrethrin can be used for flea control in small animals [see, for example 45 Wang I.-H.: Moorman R.; Burleson J. I-H. Wang, Journal of Liquid Chromatography and Related Technologies, (1996) 19/20 (3293-3304)].

Moreover, using propylene carbonate or isopropyl myristate as solvents in fipronil-containing spot-on formulations for parasite control in animals is known from WO 2009/027506 A2, wherein such formulations can also contain pyrethroids.

Furthermore, the specific combination of these two solvents is also known from WO 2008/030385 A2.

However, none of these documents yields the inventive advantageous selection of the specific active substance combination with vitamin E compounds (in particular in contents ≥10% by wt.) for the improvement of the compatibility of such preparations.

In view of this prior art, it is desirable to replace the known formulations with such formulations that have a high degree of skin compatibility and toxicological safety, are characterized by a good long-term action of several weeks, and can be applied well onto the animal.

It was now found, surprisingly, that insecticidal active substance formulations based on phenylpyrazoles, particularly in the form of combination preparations with another insecticide from the group of the pyrethroids containing vitamin E or a derivative thereof, particularly vitamin E acetate, preferably in a quantity of ≥3.0% by wt. (based on the total composition), more preferably ≥10% by wt., exhibit significantly improved effects with regard to compatibility and long-term action as compared with the known active substance formulations.

The use of tocopherols as an antioxidant in insecticidal active substance formulations is already mentioned, for example, in the above-mentioned documents GB 2135886, WO 1991/13545 or WO 2004/064522. However, they do not relate to any active substance combinations with active substances from the group of the phenylpyrazoles and the pyrethroids.

In WO 2004/064522, a content of antioxidants in the total composition of up to a maximum of 0.5% by wt. is mentioned. Higher tocopherol contents (≥3% by wt.), or especially the use of tocopheryl acetate, are not disclosed.

In the aforementioned WO 2001/35739 as well as in EP 1624756, tocopherol is also mentioned as a possible antioxidant, with combination preparations of phenylpyrazoles and pyrethroids not being the subject matter of the invention either in this case, but rather only those based on pyrethroids (flumethrin) with insecticides from other classes of active substances. However, both documents mention the possibility, in principle, of adding further combination active substances, such as those from the group of the phenylpyrazoles (e.g.) fipronil), among others. Only WO 2001/35739 lists a specific exemplary embodiment with tocopherol as an antioxidant, in which, however, the tocopherol content is only approx. 0.1% by wt., and in which only active substances from the group of the pyrethroids (flumethrin) and of the nicotinyl insecticides (thiamethoxam) are included. Moreover, both documents in principle only make mention of a possible antioxidant content of maximally 2.5% by wt. An explicit combination of active substances from the group of the phenyl pyrazoles and the pyrethroids with ≥3% by wt. vitamin E or, in particular, with vitamin E acetate, is therefore also not apparent from these documents.

WO 2010/026370 in principle also mentions tocopherol as a possible antioxidant in insecticidal active substance formulations, with the proportions of antioxidant also not exceeding a content of 1% by wt. At the same time, this document moreover relates to combination preparations based on an insect growth regulator and/or a pyrazole insecticide (e.g. fipronil) and/or a chloronicotinyl insecticide. However, a specific selection of the pyrazole insecticide such as fipronil in combination with a pyrethroid active substance and tocopherol or tocopheryl acetate is thus also not explicitly apparent from this document.

However, a combination preparation for pest control in animals comprising a phenylpyrazole (e.g. fipronil) and a pyrethroid (e.g. cyphenothrin), which can also contain antioxidants from the group of the vitamin E compounds, is known from US 2011/071193 A1 and the associated subsequent application WO 2011/038024 A1. However, no mention is made in them of deltamethrin as a possible pyrethroid. A specific combination of fipronil, deltamethrin and vitamin E acetate is also not disclosed. Furthermore, the addition of vitamin E derivatives is mentioned against the background of their antioxidative action. Though it is suggested that antioxidants may generally also cause an improvement of compatibility, however, this is neither put in relation to any specific compound group of the listed antioxidants, nor specified with regard to any specific class of active substances. Thus, no specific suggestion can be found, in particular, as to any improvement of the compatibility especially due to vitamin E derivatives (in particular vitamin E acetate) for the pyrethroids used (in particular deltamethrin, of which no mention is made here at all). From the group of the vitamin E compounds, tocopheryl nicotinate is mentioned in these documents as a preferred antioxidant, without giving any suggestion as to an improvement of the compatibility therefor.

Moreover, these documents disclose an addition of the antioxidants up to only 10% by wt. (usually less than 10% by wt.). No suggestions can be found herein for the use of higher contents. However, the inventors of the present invention surprisingly found that the advantageous effects for improving the compatibility showed themselves in particular at contents of vitamin E or vitamin E acetate from 10% by wt. or higher.

In addition, suggestions can be found in the literature as to the positive effects of vitamin E and derivatives thereof in the case of incompatibilities to insecticidal pyrethroid active substances. For example, Flannigan et al. describe in BRITISH JOURNAL OF INDUSTRIAL MEDICINE (1985; 42:363-372) that vitamin E acetate (dl-alpha-tocopheryl acetate) exhibits positive effects in the case of paresthesias which were triggered, in particular, by cyano-pyrethroid active substances, such as fenvalerate. The investigations that were presented, however, relate exclusively to intolerance reactions in humans, but not in animals, such as dogs or cats. Moreover, only an effect of the vitamin E acetate in the case of an occurrence of paresthesias is described herein. A suggestion as to corresponding positive effects while simultaneously applying other pyrethroid active substances and vitamin E acetate in a combination preparation in the sense of a prophylactic treatment is neither apparent, nor can be derived, therefrom. In particular, corresponding effects are also not mentioned in the case of the pyrethroids particularly preferred according to the invention, flumethrin and deltamethrin. In TOXICOL REV (2005; 24(2): 93-106), Bradberry et al. merely make general mention of a positive effect of a topical application of dl-alpha tocopheryl acetate in paresthesias after pyrethroid-induced damage in humans.

Moreover, Aldana et al. furthermore describe in TOXICOL LETT. (2001; 125(1-3): 107-116) that orally administered alpha-tocopheryl acetate exhibits positive effects in the case of hepatotoxic damage after i.p. application of cypermethrin (pyrethroid insecticide).

Furthermore, Malley et al. describe in TOXICOL LETT. (1985; 29(1): 51-58), that the dermal pre-treatment with vitamin E led to a reduction of fenvalerate-induced skin sensitizations in guinea pigs. No mention is made of any comparable action in the case of side effects caused by flumethrin or deltamethrin, or of a corresponding effect in the treatment of dogs and cats. There is also no suggestion as to an advantageous effect in the case of a simultaneous application of within the sense of a combination preparation.

OBJECT

Therefore, it was the object of the present invention to provide a novel agent for the control of parasites on animals which has a high degree of efficacy, particularly a high level of long-term action, with a high level of compatibility at the same time, particularly skin compatibility. Moreover, the object was to provide these novel insecticidal agents in suitable and improved active substance formulations that have a high level of compatibility, good applicability and improved long-term action, particularly if used as spot-on formulations.

DESCRIPTION OF THE INVENTION

Surprisingly, the inventors of the present invention found that the present object could be achieved by providing agents that comprise at least one active substance from the group of the phenylpyrazoles in combination with vitamin E or derivatives thereof, such as, in particular, vitamin E acetate, preferably in a quantity of ≥3.0% by wt., more preferably ≥10% by wt., still more preferably >10% by wt. (based on the total composition), as well as optionally also another active substance from the group of the pyrethroids and/or optionally further additional active and/or auxiliary substances.

So far, such improved agents and their advantageous effects were neither explicitly described nor made obvious.

The improved effects showed themselves in particular also in the further embodiment preferred within the context of the present invention, which relates to agents for the control of parasites on animals, which, in addition to at least one active substance from the group of the phenylpyrazoles in combination with vitamin E or a derivative thereof, additionally comprises at least one active substance from the group of the pyrethroids, as well as optionally further additional active and/or auxiliary substances.

Within the context of the present invention, active substances from the group of the phenylpyrazoles (also N-phenylpyrazole or N-aryl-pyrazoles) in principle include such substances as are known from US 2006/014802, WO 2005/090313, FR 2834288, WO 2009/828277, U.S. Pat. No. 6,069,157, WO 2000/31043, DE 9824487, WO 2009/804530, WO 2009/962903, EP 00933363, EP 00911329, WO 200/9856767, U.S. Pat. No. 5,814,652, WO 2009/845274, WO 1998/40359, WO 2009/828279, WO 2009/828278, DE 9650197, WO 2009/824767, EP 00846686, EP 00839809, WO 2009/728126, EP 00780378, GB 02308365, U.S. Pat. No. 5,629,335, WO 2009/639389, U.S. Pat. No. 5,556,873, EP 00659745, U.S. Pat. No. 5,321,040, EP 00511845, EP 234119, EP 295117, WO 1998/24769, U.S. Pat. No. 5,232,940, EP 295117, EP 352944, and which are herewith comprised in their entirety by the content of the disclosure.

From the group of the phenylpyrazole derivatives, fipronil (5-amino-3-cyano-1-(2,6-dichloro-4-trifluoromethyl-phenyl)-4-trifluoromethylsulphinlpyrazole) is particularly preferred.

Within the context of the present invention, active substances from the group of the pyrethroids include both natural as well as synthetic pyrethroids.

Natural pyrethroids include, in particular, pyrethrins, such as pyrethrin I and pyrethrin II as well as extracts thereof, as well as pyrethrum and derivatives thereof.

Synthetic pyrethroids include, in particular, so-called type I pyrethroids (without alpha-cyano group) and type II pyrethroids (alpha-cyano pyrethroids with alpha-cyano group) as well as non-ester pyrethroids (e.g. etofenprox). They differ from one another substantially with regard to their acute actions. In animal testing, type I leads to the so-called "T-syndrome", after the tremor that occurs. Ataxia, hyperexcitability and hypersensitivity to stimuli are also observed in the case of the "T syndrome". Type I pyrethroids include, for example Type II pyrethroids cause a "CS syndrome" which is named after the characteristic symptoms choreoathetosis (involuntary slow movements) and salivation. In addition, a coarse tremor and clonic spasms also occur in this case.

Synthetic pyrethroids include, in particular, alphamethrin, allethrin, barthrin, bioresmethrin, biopermethrin, cismethrin, cyciethrin, cypermethrin, cyhalothrin, cyfluthrin, cyphenothrin, deltamethrin, dimethrin, fenpropanate, fenvalerate, flumethrin, fluvalinate, indothrin, permethrin, phenothrin, phthalthrin, resmethrin, tetramethrin, sumithrin, tralomethrin and tralocythrin.

Type II pyrethroids (alpha-cyano pyrethroids) are particularly preferred, with deltamethrin and flumethrin being particularly preferred. Most preference is given to deltamethrin.

In another preferred embodiment, the agents according to the invention additionally comprise one or more active substances from the group of the development inhibitors.

Development inhibitors or insect growth regulators regulate the development of larvae and prevent their further development and growth into an adult pest, and thus their reproduction. Development inhibitors may come, for example, from the group of the juvenile hormones. Development inhibitors and insect growth regulators include, for example, juvenile hormones, such as azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3 (2h)-one; as well as chitin synthesis inhibitors, such as chlorofluazuron, cyromazine, diflubenzuron, fluazuron, flucycloxuron, flufenoxuron, hexaflumuron, lufenuron, tebufenozide, teflubenzuron, triflumuron. Pyriproxifen and methoprene are preferred development inhibitors.

All of the active substances mentioned within the context of the invention can additionally be defined by the internationally known designations according to "The Pesticide Manual"; 10th edition, 1994, Ed. Clive Tomlin, Great Britain.

If applicable, the active substances used according to the invention can be present, depending on the type and arrangement of the substituents, in various stereoisomeric forms, particularly as enantiomers and racemates, wherein both the pure stereoisomers as well as mixtures thereof can be used according to the invention.

Optionally, the active substances according to the invention can also be used in the form of their salts, with pharmaceutically suitable acid addition salts and basic salts being eligible, such as, for example, salts of mineral acids or organic acids (for example carboxylic acids or sulphonic acids), such as, in particular, hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. Pharmaceutically suitable basic salts include, for example, alkali metal salts, such as sodium or potassium salts, and alkaline earth metal salts, such as magnesium or calcium salts.

The active substances according to the invention can also be used in the form of their solvates, in particular hydrates, which includes both the solvates (in particular hydrates) of the active substances themselves as well as those of their salts.

Particularly preferred embodiments thus relate to:
1. Agents comprising at least one phenylpyrazole (in particular fipronil) and vitamin E or a derivative thereof (in particular vitamin E acetate), as well as optionally further active and/or auxiliary substances.
2. Agents comprising at least one phenylpyrazole (in particular fipronil) and vitamin E or a derivative thereof (in particular vitamin E acetate) and at least one pyrethroid (in particular deltamethrin or flumethrin), as well as optionally further active and/or auxiliary substances.
3. Agents according to embodiments 1 and 2, which additionally comprise at least one active substance from the group of the development inhibitors (in particular pyriproxifen or methoprene).
4, Agents according to any one of the embodiments 1 to 3, wherein the content of vitamin E or of the derivative thereof is at least 10% by wt., based on the total composition.

In this case, one embodiment is particularly preferred which comprises at least one phenylpyrazole (in particular fipronil) and ≥10% by wt. vitamin E or a derivative thereof (in particular vitamin E acetate) and at least one pyrethroid (in particular deltamethrin), as well as optionally further active and/or auxiliary substances.

According to the invention, particularly such agents are preferred which comprise a combination of fipronil and deltamethrin.

Because of the particularly advantageous effects of such an active substance combination, the present invention thus also generally comprises agents for the control of parasites on animals comprising a combination of the active substances fipronil and deltamethrin.

As was already mentioned, in particular active substances from the group of the pyrethroids, such as flumethrin and deltamethrin, too, are known for their irritating effect on the skin and the mucosa and for the occurrence of side effects in the form of skin-incompatibility reactions, such as pruritus (itching), erythema development (reddening) or paresthesias. Surprisingly, the inventors of the present invention have now found that such side effects and incompatibility reactions, which can be caused by the application or the dermal (topical, external) contact with such an active substance combination, can be significantly reduced or totally suppressed by the simultaneous administration of vitamin E, particularly vitamin E acetate (tocopheryl acetate). In this case, the action covers both local as well as systemic incompatibility reactions.

In particular, an immediate (concurrent, simultaneous) administration of the insecticidal active substances with vitamin E or vitamin E acetate in a combination preparation has proved to be particularly advantageous in this case. Because of this simultaneous combined application, the development of incompatibility reactions can be suppressed or reduced from the outset, in the sense of a prophylactic treatment, which is advantageous over a subsequent treatment in the sense of an acute treatment described in the prior art, because the incompatibility reactions, and thus damage to the affected skin or mucosal areas, have already occurred.

In particular, topical or dermal side effects, such as pruritus (itching) and erythema development (reddening) as well as alopecia and also an increased salivation of the mucosa can be reduced by means of the combination of the pyrazole derivatives and the pyrethroids with vitamin E (vitamin E acetate) according to the invention. Such an effect, in particular the positive effect of reducing topical side effects such as pruritus and reddening, alopecia and salivation, of vitamin E during pyrethroid application was hitherto unknown and not made obvious in the prior art.

Within the context of the present invention, the term vitamin E comprises the group of all vitamin E compounds discovered so far. These are fat-soluble substances with frequently antioxidative actions. Vitamin E is a constituent of the membranes of animal cells but is formed only by photosynthetically active organisms such as plants and cyanobacteria. Four of the forms of vitamin E known so far are also referred to as tocopherols. Four other forms of vitamin E are referred to as tocotrienols or 13. Moreover, there are also tocomonoenols (T1) and MDT (marine-derived tocopherols). Alpha-tocopherol ((2R)-2,5,7,8-tetramethyl-2-[(4R,8R)-4,8,12-trimethyltridecyl]-3,4-dihydro-2H-chromen-6-ol) is the most comprehensively investigated form of vitamin E:

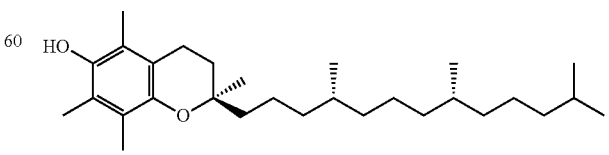

RRR-Isomer

Other forms are beta-tocopherols, gamma-tocopherols and delta-tocopherols. The tocotrienols, tocomonoenols and MDTs can also be provided in an alpha-, beta-, gamma- or delta form. Furthermore, all stereoisomers as well as mixtures thereof are comprised according to the invention.

Within the context of the present invention, vitamin E derivatives in particular relate to glycosides, esters, salts and complexes of vitamin E. Esters of vitamin E, such as, in particular, vitamin E acetate or tocopherol acetate or tocopheryl acetate (in particular alpha-tocopheryl acetate) are particularly preferred.

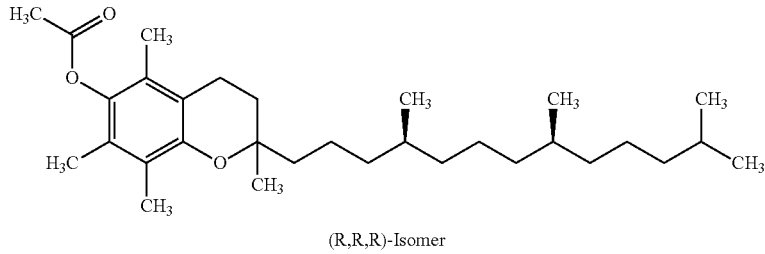 [SMILES: CC(=O)Oc1c(C)c(C)c2c(c1C)CCC(C)(CCC[C@@H](C)CCC[C@@H](C)CCCC(C)C)O2]

(R,R,R)-Isomer

Alpha-tocopheryl acetate (vitamin E acetate) is a synthetic vitamin E derivative which belongs to the group of the so-called provitamins. The three stereocenters of alpha-tocopheryl acetate result in eight stereoisomeric alpha-tocopheryl acetates. All eight stereoisomers as well as mixtures thereof, such as dl-alpha-tocopheryl acetate, are comprised according to the invention. Furthermore, there are beta-gamma, and delta forms, each with eight stereoisomers, also of tocopheryl acetate.

Within the context of the present invention, vitamin E acetate or tocopheryl acetate (in particular alpha-tocopheryl acetate) is particularly preferred.

Within the context of the present invention, particularly such combination preparations are preferred in which the use of tocopherol nicotinate from the group of the vitamin E derivatives is excluded.

According to the invention, comparatively high contents of vitamin E or derivatives thereof, such as, in particular, vitamin E acetate, in the agents according to the invention have proved particularly effective. Antioxidants are usually used in insecticidal active substance formulations in significantly lower quantities up to approximately 2.5% by wt., or up to maximally 10% by wt., wherein, if vitamin E, for example, is used as an antioxidant, it is also usually used in contents of significantly less than 1% by wt.

According to the invention, vitamin E or its derivatives are preferably used in a quantity ≥3% by wt., more preferably ≥5% by wt., still more preferably ≥7% by wt., most preferably ≥10% by wt., in each case based on the total composition, in the agents according to the invention, for example in agents according to the preceding embodiments 1., 2. and 3.

It is very much preferred to use a content of vitamin E or its derivatives of >10% by wt., because the improvement of the compatibility desired according to the invention is thereby obtained particularly well. Moreover, it is further preferred to use a vitamin E content of ≥12% by wt., more preferably ≥15% by wt., more preferably ≥18% by wt., still more preferably ≥20% by wt.

Within the context of the present invention, it was also surprisingly found that a further improvement of the compatibility and efficacy of the active substance combination according to the invention can be attained particularly by using a specific active substance formulation based on a combination of an aliphatic cyclic carbonate and a spreading agent.

Aliphatic cyclic carbonates include, in particular, ethylene carbonate, propylene carbonate and mixtures thereof, with propylene carbonate being preferred.

Spreading agents include, for example, surface active agents, such as surfactants, such as anionic surfactants (e.g. sodium laurylsulfate, fatty alcohol ether sulfates and monoethanolamine salts of mono-/di-alkylpolyglycolether orthophosphoric acid esters), cationic surfactants (e.g. cetyl trimethyl ammonium chloride) amphoteric surfactants (e.g. di-sodium-N-laurylaminodipropionate or lecithin), and nonionic surfactants (e.g. polyoxyethylated castor oil, polyoxyethylated sorbitane monooleate, sorbitane monostearate, ethylalcohol, glycerol monosterate, polyoxyethylene stearate and alkylphenol polyglycol ether) as well as, in particular, polymeric surfactants, for example those based on polymethoxysiloxanes, silicones, fats and oils, such as, for example, silicone oils of different viscosities; fatty acid esters such as ehtylstearate, di-n-butylester, lauric acid hexylester, dipropylene glycol pelargonate, esters of a branched fatty acid with a medium chain length and saturated C16-C18 fatty alcohols, isopropyl myristate, isopropyl palmitate, caprylic/capric acid esters from saturated fatty alcohols with a chain length of C12-C18, isopropyl stearate, oleic acid oleyl ester, oleic acid decyl ester, ethyloleate, lactic acid ethyl ester, wax-like fatty acid esters, dibutyl phthalate, adipic acid diisopropyl esters and ester mixtures; triglycerides based on oleic acid, palmitic acid, linoleic acid, stearic acid, caprylic acid and capric acid, such as in particular caprylic/capric acid triglyceride, triglyceride mixtures with vegetable fatty acids with a chain length of C8-C12 or other especially selected natural fatty acids, partial glyceride mixtures of saturated and unsaturated fatty acids and mono and/or diglycerides of the C8-/C10-fatty acids; fatty alcohols, such as isotridecyl alcohol, 2-octyldodecanol, cetylstearyl alcohol and oleyl alcohol; fatty acids, such as oleic acid, palmitic acid, linoleic acid, stearic acid, caprylic acid and capric acid, lactones, such as butyrolactone; phospholipids and phosphatidylcholines etc.

Fatty acid esters are particularly preferred spreading agents, with isopropyl myristate being selected with particular preference.

Thus, the above-mentioned embodiments 1., 2., 3. and 4. are particularly preferred according to the invention, which are present in an active substance formulation comprising a combination of aliphatic cyclic carbonate (particularly propylene carbonate) and at least one spreading agent from the group of the fatty acid esters (particularly isopropyl myristate).

In this case, the specific selection of a combination of propylene carbonate and a fatty acid ester, such as isopropyl myristate, has in this case proved to be particularly suitable. On the one hand, good solubility of the selected active substance combination can be attained by means of the propylene carbonate. However, only insufficient spreading and applicability is provided due to the high polarity of the propylene carbonate. By specifically selecting the spreading agent isopropyl myristate, an optimum stabilization of the active substance formulation, and thus an improvement of the spreadability, could be obtained, which is advantageous compared with other known spreading agents, such as, in particular, compared with silicones or polysiloxanes, non-ionic surfactants or phosphatidylcholine, in that there is no crystallization of the formulation and thus no local overdosage at the immediate location of the application. Apart from improving compatibility, good spreadability moreover has an advantageous effect on the long-term action, as was shown in the following examples.

The use of aliphatic cyclic carbonates, such as propylene carbonate, as well as of spreading agents, such as also fatty acid esters, such as isopropyl myristate, in insecticidal active substance formulations is known in principle from the prior art, e.g. from WO 2001/35739 and DE 19954394, which describe active substance formulations based on polysiloxanes that can also contain, among others, propylene carbonates, but which offer no suggestions as to spreading agents, such as fatty acid esters, in particular isopropyl myristate, or generally also from EP 1624756. A specific combination of propylene carbonate with isopropyl myristate, or even of this combination with the specific combination according to the present invention is not apparent from any of these documents.

DE 102006061538, or WO 2008/080542, and GB 2457734 also mention cyclic carbonates as possible ingredients of the formulation, namely in combination with aliphatic cyclic or acyclic polyethers, with DE 102006061538, or WO 2008/080542, comprising as spreading agents those from the group of the polysiloxanes, whereas GB 2457734 mentions neither spreading agents from the group of the silicones/polysiloxanes, nor from the group of the fatty acid esters. No mention at all is made of the use of tocopherol in any of these cases.

The use of spreading agents from the group of the silicones or polysiloxanes is disadvantageous due to the above-described instability of the formulation if applied on the animal.

The use of aliphatic cyclic or acyclic polyethers is disadvantageous because they constitute comparatively polar compounds that adversely affect the spreading behavior of the active substance formulation, which in turn is disadvantageous with regard to the compatibility of the formulation. Accordingly, those active substance formulations or agents are particularly preferred, according to the invention, in which the use of spreading agents from the group of the silicones or polysiloxanes and/or aliphatic cyclic or acyclic polyethers is excluded.

In the improved active substance formulations according to the invention, the active substances can be contained in the following quantities:

Phenylpyrazoles in a quantity of at least 1.0% by wt., more preferably at least 3.0% by wt., still more preferably at least 5.0% by wt., especially preferably at least 7.0% by wt., or in a quantity of up to 20.0% by wt., more preferably up to 17.0% by wt., still more preferably up to 15.0% by wt., especially preferably up to 12.0% by wt;

Pyrethroids in a quantity of at least 0.05% by wt., more preferably at least 0.1% by wt., still more preferably at least 0.2% by wt., especially preferably at least 0.3% by wt., or in a quantity of up to 7.0% by wt., more preferably up to 5.0% by wt., still more preferably up to 3.0% by wt., especially preferably up to 1.5% by wt.

The following active substance ranges are particularly preferred: Phenylpyrazoles: 1.0 to 20.0% by wt., more preferably 3.0 to 17.0% by wt., still more preferably 5.0 to 15.0% by wt., especially preferably 7.0 to 12.0% by wt., and Pyrethroids: 0.05 to 7.0% by wt., more preferably 0.1 to 5.0% by wt., still more preferably 0.2 to 3.0% by wt., especially preferably 0.3 to 1.5% by wt.

Particularly, because of the present invention it is possible, on the one hand, that, while comparatively large quantities of active substances are used, a high level of compatibility is nevertheless achieved by means of the combination with vitamin E (or its derivatives).

On the other hand, however, even if comparatively small quantities of active substances are used, which is accompanied by a better compatibility, a sufficient or good action (in particular long-term action) can be achieved especially by using the active substance formulation preferred according to the invention, due to its good applicability and spreadability on the animal to be treated.

Furthermore, the agents according to the invention can contain customary auxiliary substances, such as, in particular, solvents, solubility promoters, synergists for the active substances according to the invention, antioxidants, preservatives, stabilizers, pH-adjusting agents, fillers, crystallization inhibitors, colorants, etc.

Possible solvents include, in particular, aromatic alcohols, such as benzyl alcohol, cyclic carbonates, such as propylene carbonate and ethylene carbonate, pyrrolidones, such as pyrrolidone-2, N-methylpyrrolidone, N-octyl-, N-butylpyrrolidone, low-boiling alcohols, such as isopropanol, ethanol, higher alcohols, such as n-octyl alcohol, lanolin alcohol and n-butanol, cyclic and acyclic ketones, such as acetone, methyl ethyl ketone and cyclohexanone, glycols, such as ethylene glycol and propylene glycol, aliphatic cyclic or acyclic ethers, such as tetrahydrofurfuryl alcohol, diethylene glycol monoethyl ether, dipropylene glycol monopropyl ether and glycofurol, benzyl benzoate, etc. Aliphatic cyclic carbonates, such as, in particular, propylene carbonate, ethanol, benzyl alcohol and benzyl benzoate are preferred. Propylene carbonate is most particularly preferred.

Stabilizers and antioxidants which may be mentioned are sulphites or metabisulphites, such as potassium metabisulphite; organic acids, such as citric acid, ascorbic acid, malic acid; phenols, butylhydroxytoluene (BHT), butylhydroxyanisole, vitamin e (tocopherols), etc.

The agents according to the invention are environmentally compatible and user-friendly due to the very low level of toxicity.

The agents according to the invention are suitable for the control of parasitic insects that occur in the keeping and breeding of animals in pets and useful animals, as well as in zoo animals, laboratory animals, test animals and hobby animals. They are effective particularly against parasitic pests selected from the group of the ectoparasites, such as insects and mites (e.g. lice, ticks, flies, mites, fleas, sand flies etc), in particular including, for example:

from the order of the Anoplura, for example, *Haematopinus* spp., *Linognathus* spp., *Solenopotes* spp., *Pediculus* spp., *Pthirus* spp.; from the order of the Mallophaga, for example, *Trimenopon* spp., *Menopon* spp., *Eomenacanthus* spp., *Menacanthus* spp., *Trichodectes* spp., *Felicola* spp.,

*Damalinea* spp., *Bovicola* spp; from the order of the Diptera, suborder Brachycera, for example, *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Crysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp;

from the order of the Diptera, suborder Nematocera, for example, *Culex* spp., *Aedes* spp., *Anopheles* spp., *Culicoides* spp., *Phlebotomus* spp., *Simulium* spp.;

from the order of the Siphonaptera, for example, *Ctenocephalides* spp., *Echidnophaga* spp., *Ceratophyllus* spp., *Pulex* spp.;

from the order of the Metastigmata, for example, *Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.;

from the order of the Mesostigmata, for example *Dermanyssus* spp., *Ornithonyssus* spp., *Pneumonyssus* spp.;

from the order of the Prostigmata, for example *Cheyletiella* spp., *Psorergates* spp., *Myobia* spp., *Demodex* spp., *Neotrombicula* spp.;

from the order of the Astigmata, for example, *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp., *Cytodites* spp., *Laminosioptes* spp.

Particularly preferred, according to the invention, is the control of parasitic insects from the group of the ectoparasites, such as, in particular, ticks, fleas and sand flies.

Accordingly, a preferred embodiment relates to agents according to the present invention for use in the prophylactic or acute treatment against ectoparasites, in particular against ticks, fleas and sand flies.

Within the context of the present invention, the term useful and breeding animals includes, for example, cattle, horses, sheep, pigs, goats, camels, water buffalo, donkeys, rabbits, fallow deer, reindeer, fur-bearing animals, such as, for example, mink, chinchilla, raccoon, birds, such as, for example, hens, geese, turkeys, ducks, etc.

According to the invention, the term hobby animals and pets, as well as laboratory and test animals includes, for example, mice, rats, guinea pigs, golden hamsters, dogs, cats and ferrets.

Preferably, the agents according to the invention are provided for use in the treatment of dogs, cats and ferrets.

In this case, application can take place both prophylactically and therapeutically, or for acute treatment.

Accordingly, another preferred embodiment relates to agents according to the present invention for use in the prophylactic or acute treatment of dogs, cats and ferrets.

According to the invention, application on the animal takes place directly or preferably in the form of suitable preparations, such as, in particular, the active substance formulations according to the invention.

A skin contact that is as good and extensive as possible is in this case advantageous for optimal action, in particular the repellent action of the pyrethroid active substances.

The use of the agents according to the invention for the external, topical or dermal use is particularly preferred.

Suitable preparations therefor are solutions or concentrates for administration after dilution for use on the skin or in body cavities, infusion formulations, gels, emulsions and suspensions, semi-solid preparations, such as formulations in which the active substance is processed in an ointment base or in an oil-in-water or water-in-oil emulsion base, solid preparations such as powders, premixes or concentrates, granulates, pellets, aerosols and active substance-containing molded bodies, which are used, for example, by dissolving and optionally diluting them for use on the skin etc. According to the invention, application preferably takes place by spraying, pouring, dripping or by application via collars for cats or dogs or ferrets.

In particular, the use as a spot-on or pour-on formulation as well as the application via active substance collars is preferred according to the invention.

According to the invention, the use of the above-described novel compounds for the control of parasites, such as, in particular, ectoparasites, particularly of ticks, fleas and sand flies, for example by application on and treatment of equipment from the keeping of animals, such as, for example, animal baskets, padding, brushes, cages, stables, etc., is comprised. In this case, the use may also take place both for the prophylactic as well as for the acute treatment.

To prepare the agents according to the invention, appropriate amounts of the desired components are mixed with one another in accordance with known methods using, for example, conventional stirring tanks or other suitable devices.

The invention is illustrated in more detail by the following examples. The examples merely constitute exemplifications, and the person skilled in the art is capable of extending the specific examples to other embodiments for which protection is sought.

EXAMPLES

1. Preparation Examples (Agents According to the Invention)

Spot-on Formulation with Fipronil, Deltamethrin and Vitamin E Acetate

Composition:

| Preparation example 1 (BF-006) | |
|---|---|
| Fipronil | 10.0% |
| Deltamethrin | 1.0% |
| Vitamin E acetate | 10.0% |
| Propylene carbonate | 35.0% |
| Isopropyl myristate | 15.0% |
| Ethanol | 9.0% |
| Benzyl benzoate | 12.5% |
| Benzyl alcohol | 7.5% |
| Preparation example 2 (BF-006.1) | |
| Fipronil | 10.0% |
| Deltamethrin | 0.2% |
| Vitamin E acetate | 10.0% |
| Propylene carbonate | 35.8% |
| Isopropyl myristate | 15.0% |
| Ethanol | 9.0% |
| Benzyl benzoate | 12.5% |
| Benzyl alcohol | 7.5% |
| Preparation example 3 (BF-006.2) | |
| Fipronil | 10.0% |
| Vitamin E acetate | 10.0% |
| Propylene carbonate | 36.0% |
| Isopropyl myristate | 15.0% |
| Ethanol | 9.0% |

| | |
|---|---|
| Benzyl benzoate | 12.5% |
| Benzyl alcohol | 7.5% |■
| Preparation example 4 (BF-006.4) | |
| Fipronil | 10.0% |
| Deltamethrin | 0.4% |
| Vitamin E acetate | 15.0% |
| Propylene carbonate | 32.6% |
| Isopropyl myristate | 13.0% |
| Ethanol | 9.0% |
| Benzyl benzoate | 12.5% |
| Benzyl alcohol | 7.5% |
| Preparation example 5 (BF-006.5) | |
| Fipronil | 10.0% |
| Deltamethrin | 0.4% |
| Vitamin E acetate | 18.0% |
| Propylene carbonate | 30.6% |
| Isopropyl myristate | 12.0% |
| Ethanol | 9.0% |
| Benzyl benzoate | 12.5% |
| Benzyl alcohol | 7.5% |

The preparation of the compositions took place in each case by mixing the individual constituents with one another until a clear, single-phase liquid was obtained.

2. Comparison Formulations

The following comparison formulations were obtained in an analogous manner:

| | Comparison 1 | Comparison 2 | Comparison 3 | Comparison 4 | Comparison 5 | Comparison 6 |
|---|---|---|---|---|---|---|
| Fipronil | 10% | 10% | 10% | 10% | 10% | 10% |
| Deltamethrin | 1% | 1% | 1% | 1% | 1% | 1% |
| Vitamin E acetate | — | — | — | — | — | — |
| BHT | — | 2% | — | — | — | 2% |
| Propylene carbonate | 89% | 73% | 10% | 40% | 40% | 87% |
| Isopropyl myristate | — | — | — | 15% | 15% | — |
| Cyclomethicone 5NF (Silicone/polysiloxane) | — | 10% | 26% | — | — | — |
| Abil B8832 (non-ionic surfactant/silicone) | — | 4% | — | — | — | — |
| Phosal 53 MCT (Phosphatidylcholine) | — | — | 34% | — | — | — |
| Ethanol | — | — | 19% | 19% | 9% | — |
| Benzyl benzoate | — | — | — | 15% | 15% | — |
| Benzyl alcohol | — | — | — | — | 10% | — |

3. Stability of the Formulation and Spreading Behavior (Applicability)

Comparison Formulation 2

0.1 ml/kg of the formulation from comparison formulation No. 2 are applied between the shoulder blades of a laboratory dog. Crystals on the hair tips became evident on the application site after approx. 2 hours. The formulation does not transport the active substances over the entire animal, the active substances concentrate at the application site.

Comparison Formulation 3

0.1 ml/kg of the formulation from comparison formulation No. 3 are applied between the shoulder blades of a laboratory dog. Crystals on the hair tips became evident on the application site after approx. 2 hours. The formulation does not transport the active substances over the entire animal, the active substances concentrate at the application site.

Preparation Example 1

0.1 ml/kg of the formulation BF-006 according to the invention are applied between the shoulder blades of a laboratory dog. The solution spreads completely over the entire animal immediately after application. Crystals are not observed at any point in time.

Result:

It was found that the known spreading agents from the group of the silicones/polysiloxanes, surfactants and phosphatidylcholine are not suitable for the active substance combination selected according to the invention in order to make possible a formulation with a good applicability and high degree of spreadability on the animal. For optimal compatibility and long-term action of the active substance formulation, optimal spreading is of importance inasmuch as crystallization and concentration of the active and auxiliary substances at the application site leads to a local overdosage and thus poorer compatibility and lower long-term action, as was observed in the case of the comparison formulations.

4. Proof of Efficacy

Efficacy Against Fleas and Ticks

Six cats were randomized into two groups and infested on day −1 with approx. 100 fleas and 50 live adult ticks. On day 0, three cats (Nos. 149, 96 und 168) were treated with the spot-on formulation BF-006.1 according to preparation example 2 (0.1 ml/kg animal body weight), three animals (Nos. 66, 53 and 47) served as untreated controls.

Reinfestations, i.e. renewed infestations with fleas and ticks were carried out on the following days: day 5, day 12, day 19 and day 26.

On the following days, all six cats were combed and examined for infestation by fleas and ticks: day 2, day 7, day 14, day 21 and day 28.

The infestation figures as well as the efficacies are represented in Table 1 (flea) and Table 2 (tick):

TABLE 1

Efficacy against Fleas

| | Number of live fleas on the animal | | | | |
|---|---|---|---|---|---|
| Cat No. | Day 2 | Day 7 | Day 14 | Day 21 | Day 28 |
| 149 | 1 | 0 | 0 | 0 | 2 |
| 96 | 0 | 0 | 0 | 0 | 11 |
| 168 | 0 | 0 | 0 | 0 | 0 |
| 66 | 81 | 84 | 91 | 10 | 91 |
| 53 | 67 | 73 | 87 | 79 | 93 |
| 47 | 79 | 71 | 78 | 67 | 58 |
| Efficacy in % | 99.6 | 100 | 100 | 100 | 94.6 |

TABLE 2

Efficacy against Ticks

| Cat No. | Number of live sucking ticks on the animal | | | | |
|---|---|---|---|---|---|
| | Day 2 | Day 7 | Day 14 | Day 21 | Day 28 |
| 149 | 0 | 0 | 0 | 0 | 0 |
| 96 | 1 | 3 | 0 | 0 | 1 |
| 168 | 0 | 0 | 0 | 0 | 0 |
| 66 | 0 | 5 | 22 | 7 | 3 |
| 53 | 0 | 2 | 13 | 13 | 24 |
| 47 | 1 | 3 | 4 | 4 | 1 |
| Efficacy in % | 0 | 70 | 100 | 100 | 96.4 |

5. Investigation of Compatibility

Six dogs and six cats were examined with regard to the local and systemic compatibility of the active substance combination according to the invention with and without vitamin E.

Three dogs and three cats, respectively, were given the spot-on BF-006 (in accordance with preparation example 1) with vitamin E (0.3 ml/kg animal body weight), three dogs and three cats, respectively, were given the corresponding spot-on without vitamin E.

Then, all animals were observed and examined after 30', 1 h, 2 h, 4 h, 8 h, 12 h and 24 h with regard to the local and systemic compatibility of the spot-on formulations.

Table 3 shows the compatibilities in summary of the dogs, Table 4 those of the cats:

TABLE 3

Compatibility Dog

| Dog No. | Spot on | Systemic compatibility | Local compatibility after 24 h |
|---|---|---|---|
| 42 | Without Vitamin E (VF005, 0.3 ml/kg) | Itching: ++ after 2 h | Reddened: ++; Alopecia approximate size of a 50 cent coin |
| 44 | | Itching: + after 4 h | Reddened: +; |
| 45 | | Itching: +++ after 30'; strong salivation | Reddened: +; Alopecia approximate size of a 50 cent coin |
| 36 | With 10% Vitamin E (BF-006, 0.3 ml/kg) | good | good |
| 47 | | good | good |
| 51 | | good | good |

TABLE 4

Compatibility Cat

| Cat No. | Spot on | Systemic compatibility | Local compatibility after 24 h |
|---|---|---|---|
| 22 | Without Vitamin E (VF005, 0.3 ml/kg) | Itching: + after 30' | Reddened: ++ |
| 27 | | good, slight salivation | Reddened: +; |
| 39 | | Itching: ++ after 2 h; strong salivation | Reddened: ++; Alopecia approximate size of a 2 € coin |

TABLE 4-continued

Compatibility Cat

| Cat No. | Spot on | Systemic compatibility | Local compatibility after 24 h |
|---|---|---|---|
| 25 | With 10% Vitamin E (BF-006, 0.3 ml/kg) | good | good |
| 29 | | good, slight salivation | good |
| 31 | | good | good |

+ slight
++ medium
+++ strong

6. Comparison Tests Against the Prior Art

Comparison with Compositions according to the Prior Art (US 2011/0071193)

Formulation According to the Invention BF-006.3 (#1)

| | wt in (%) |
|---|---|
| Fipronil | 10.0 |
| Deltamethrin | 0.4 |
| Propylene carbonate | 35.6 |
| Ethanol | 9.0 |
| Isopropyl myristate | 15.0 |
| Benzyl benzoate | 12.5 |
| Benzyl alcohol | 7.5 |
| Vitamin E acetate | 10.0 |

Dosage 0.1 ml/kg animal body weight
Formulation according to Prior Art (in analogy to US2011/0071193 A1) (#2)

| | wt in (%) |
|---|---|
| Fipronil | 10.0 |
| Cyphentoin | 0.4 |
| Vitamin E nicotinate | 0.5 |
| Diethylene glycol monoethyl ether | 89.1 |

Dosage 0.1 ml/kg animal body weight
Test Application of the Two Formulations #1 and #2 on Cats
Dosage 0.3 ml/kg

| | after 24 h | | after 48 h | | after 72 h | |
|---|---|---|---|---|---|---|
| Formulation | #1 | #2 | #1 | #2 | #1 | #2 |
| Cat 1/1.35 ml | | | | | | |
| Application site visible | Yes | Yes | No | Yes | No | Yes |
| Hairs stuck together | Yes | Yes | No | Yes | No | Yes |
| Crystals of active substance on application site | No | No | No | Yes | No | Yes |
| Cat 2/1.50 ml | | | | | | |
| Application site visible | Yes | Yes | No | Yes | No | Yes |
| Hairs stuck together | Yes | Yes | No | Yes | No | Yes |
| Crystals of active substance on application site | No | Yes | No | Yes | No | Yes |
| Cat 3/1.80 ml | | | | | | |
| Application site visible | Yes | Yes | Yes | Yes | No | Yes |

-continued

|  | after 24 h | | after 48 h | | after 72 h | |
|---|---|---|---|---|---|---|
| Formulation | #1 | #2 | #1 | #2 | #1 | #2 |
| Hairs stuck together | Yes | Yes | Yes | Yes | No | Yes |
| Crystals of active substance on application site | No | Yes | No | Yes | No | Yes |

With these data, it becomes clear that the formulation according to the invention BF-006.3 (#1), compared to the formulation in analogy to US 2011/0071193 A1 (#2), in particular has the following decisive advantages:
1. The active substance-containing solution spreads significantly better over the animal, so that this also results in a better distribution of the active substance, which ensures a greater protection of the animal and also leads to better compatibility because the active substances are distributed over a larger surface.
2. The formulation in analogy to US 2011/0071193 A1 (#2) has a strong tendency to crystallize. Active substance crystals, which can be found in the tips of the hairs, form on the application site after 24 h at the latest. Due to the crystallization, the distribution of the active substances over the animal is no longer complete, which means that the dosage falls below the effective dose. Furthermore, this causes an increased danger of contamination for the owner of the animal.

The invention claimed is:
1. An agent for the control of ticks, fleas and sand-flies on animals, consisting of:
   1 to 20% by wt. fipronil,
   0.05 to 7% by wt. deltamethrin,
   10 to 20% by wt. vitamin E acetate or alpha-tocopheryl acetate,
   30 to 36% by wt. propylene carbonate,
   12 to 15% by wt. isopropyl myristate, and
   7.5 to 20% by wt. of at least one solvent.
2. An agent for the control of ticks, fleas and sand-flies on animals, consisting of
   1 to 20% by wt. fipronil,
   0.05 to 7% by wt. deltamethrin,
   10 to 20% by wt. vitamin E acetate or alpha-tocopheryl acetate,
   30 to 36% by wt. propylene carbonate,
   12 to 15% by wt. isopropyl myristate,
   7.5 to 20% by wt. of at least one solvent; and
   synergists for the active substances fipronil and deltamethrin.
3. A spot-on formulation comprising the agent as defined in claim 1.
4. A spot-on formulation comprising the agent as defined in claim 2.
5. A method of reducing at least one condition selected from the group consisting of pruritis, itching, erythema, skin reddening, alopecia and increased salivation in animals, to be treated to control ticks and fleas and/or sand-flies, the method comprising topically applying the agent according to claim 1.
6. The method according to claim 5, wherein the animal is selected from dogs, cats and ferrets.
7. A method of reducing at least one condition selected from the group consisting of pruritis, itching, erythema, skin reddening, alopecia and increased salivation in animals, to be treated to control ticks and fleas and/or sand-flies, the method comprising topically applying the agent according to claim 2.
8. The method according to claim 7, wherein the animal is selected from dogs, cats and ferrets.

* * * * *